US011013498B2

(12) United States Patent
Schwintner et al.

(10) Patent No.: US 11,013,498 B2
(45) Date of Patent: May 25, 2021

(54) MICROORGANISM SAMPLING METHOD, MICROORGANISM SAMPLING DEVICE AND SAMPLING KIT COMPRISING SUCH A SAMPLING DEVICE

(71) Applicants: MAAT PHARMA, Lyons (FR); INSTITUT NATIONAL DE LA RECHERCHE AGRONOMIQUE, Paris (FR)

(72) Inventors: Carole Schwintner, Lyons (FR); Hervé Affagard, Lyons (FR); Joël Dore, Vitry-sur-Seine (FR)

(73) Assignees: MAAT PHARMA, Lyons (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 182 days.

(21) Appl. No.: 15/568,932

(22) PCT Filed: Apr. 22, 2016

(86) PCT No.: PCT/FR2016/050963
§ 371 (c)(1),
(2) Date: Oct. 24, 2017

(87) PCT Pub. No.: WO2016/170290
PCT Pub. Date: Oct. 27, 2016

(65) Prior Publication Data
US 2018/0116641 A1 May 3, 2018

(30) Foreign Application Priority Data
Apr. 24, 2015 (FR) ...................................... 1553721

(51) Int. Cl.
*A61B 10/00* (2006.01)
*G01N 1/10* (2006.01)

(52) U.S. Cl.
CPC ...... *A61B 10/0038* (2013.01); *A61B 10/0096* (2013.01); *G01N 1/10* (2013.01); *G01N 2001/1025* (2013.01)

(58) Field of Classification Search
CPC .. A61B 10/0038; A61B 10/0096; G01N 1/10; G01N 2001/1025
See application file for complete search history.

(56) References Cited

U.S. PATENT DOCUMENTS

2015/0037285 A1   2/2015 Blaser et al.

FOREIGN PATENT DOCUMENTS

EP   2552321      2/2013
WO   02/07741     1/2002
(Continued)

OTHER PUBLICATIONS

Tauxe, et al. "Fecal Microbiota Transplant Protocol for Clostridium Difficile Infection," Lab Medicine, 2015, vol. 46, No. 1, pp. 1-8.
(Continued)

*Primary Examiner* — Gautam Prakash
*Assistant Examiner* — Lydia Edwards
(74) *Attorney, Agent, or Firm* — Browdy and Neimark, PLLC

(57) ABSTRACT

A sampling method using a sampling device (2) comprising a container (5) comprising a body (6) consisting of a soft pouch, and a lid (30), in which at least one among the container (5) and the lid (30) is provided with a discharging member (40) suitable for, in an open state, discharging at least one part of the gases contained in the internal space (7) of the body (6) of the container (5), wherein the sampling method comprises the steps consisting in: —collecting a biological material in the body (6) of the container (5), and assembling the lid (30) on the neck (10) of the container (5), —and placing an internal space (7) of the body (6) of the
(Continued)

container (5) under anaerobic conditions by placing the discharging member (40) in the open state, by compressing the body (6) of the container (5) and by placing the discharging member (40) in a closed state.

5 Claims, 3 Drawing Sheets

(56) References Cited

FOREIGN PATENT DOCUMENTS

| WO | 2011/122949 | 10/2011 | |
| WO | 2012/016287 | 2/2012 | |
| WO | 2012/122478 | 9/2012 | |
| WO | WO-2013090825 A1 * | 6/2013 | ............ A61J 1/00 |
| WO | 2014/078911 | 5/2014 | |
| WO | 2014/121298 | 8/2014 | |
| WO | 2014/121301 | 8/2014 | |
| WO | 2014/121302 | 8/2014 | |
| WO | 2014/121304 | 8/2014 | |
| WO | 2014/176632 | 11/2014 | |
| WO | 2014/197562 | 12/2014 | |
| WO | 2016/201114 | 12/2016 | |
| WO | 2017/075098 | 5/2017 | |

OTHER PUBLICATIONS

Everard, et al., Cross-talk between Akkermansia muciniphila and intestinal epithelium controls diet-induced obesity, Proc. Natl. Acad. Sci, USA, May 2013, pp. 9066-9077, vol. 110, No. 22.

Sokol, et al., Faecalibacterium prausnitzii is an anti-inflammatory commensal bacterium identified by gut microbiota analysis of Crohn disease patients, Proc. Natl. Acad. Sci. USA, Oct. 2008, pp. 16731-16736, vol. 105 No. 43.

* cited by examiner

MICROORGANISM SAMPLING METHOD, MICROORGANISM SAMPLING DEVICE AND SAMPLING KIT COMPRISING SUCH A SAMPLING DEVICE

FIELD OF THE INVENTION

The invention relates to a microorganism sampling method, a microorganism sampling device and a sampling kit employing such a sampling device The invention applies in particular to the sampling of human intestinal microbiota for example for testing intestinal dysbioses, such as infections of *Clostridium difficile*, by transportation of the intestinal microbiota.

BACKGROUND OF THE INVENTION

The intestinal microbiota is constituted by the group of all microorganisms (bacteria, yeast and fungi) to be found in the human gastro-intestinal tract (intestine, stomach and stools). The microbial diversity is currently estimated at about $10^3$ bacterial species composing the dominant intestinal microbiota of an adult individual, with an abundance of $10^{14}$ bacteria, representing a bacterial metagenome of 200 000 to 800 000 genes in each individual, which is 10 to 50 times the number of genes of the human genome.

The intestines are sterile in utero and are colonized as of the first days of life to develop towards a unique individual microbiota. Each person has bacteria that are relatively close in terms of species, but the exact composition of his or her microbiota (species, proportions) is to a large extent (about ⅔ of the species) specific to the host.

Thus, the human intestinal microbiota is a very diversified ecosystem, which is complex and specific to each individual.

It is essential for the health of an individual to maintain a stable microbiota which is both capable of returning to its initial state after a change and resistant to invasion. Maintaining a wide diversity of microbiota promotes its stability.

However, certain pathologies or treatments unbalance the microbiota: for example, antibiotics as well as diseases with an inflammatory component, such as inflammatory bowel disease (IBD), can limit the diversity of the microbiota in the intestines. Antibiotics treatments (or antibiotic therapy), in particular, result in an alteration of the microbiota, which can promote the proliferation of pathogenic organisms such as *Clostridium difficile*. Infections of *Clostridium difficile* are responsible for nosocomial diarrhea; this bacterium is resistant to conventional antibiotic therapy (of broad spectrum, such as vancomycin and metronidazole).

In order to reestablish the intestinal flora, and fight against infections of *Clostridium difficile* type, and thereby reestablish homeostasis (i.e. symbiosis), a transplantation of faecal microbiota has been envisioned and tested. It consists in the introduction of the stools of a healthy donor subject into the digestive tract of a recipient patient, in order to re-balance the altered intestinal flora of the host. This transplantation of faecal microbiota can be allogenic (that is to say from a healthy donor individual to a patient) or autologous (that is to say from an individual to himself). The results obtained on infections of *Clostridium difficile* type are encouraging, and some patients have been successfully treated (Tauxe et al, Lab Medicine, Winter 2015, volume 46, Number 1).

Prior to performing such a transplantation, the microbiota is generally sampled from the healthy donor subject through use of a sampling device of the type comprising:

a container comprising a body which comprises an internal space configured to receive the biological matter, and a neck which delimits an access opening to the internal space of the body, the body of the container being constituted by a flexible bag, a cover configured to be removably and sealingly mounted on the neck of the container so as to obturate the access opening of the neck and close the internal space of the body, a transfer member internally comprising a passage between the internal space and an external environment, the transfer member having an open state in which said transfer member establishes communication with the internal space through the passage, and a closed state in which said transfer member prevents all communication with the internal space through the passage.

A known sampling device of this type is described in document WO 2013/090825. With such a sampling device, after having collected the biological matter, the container is closed with the cover before placing the biological matter in suspension by mixing the collected biological matter with a diluent fluid. Anaerobic conditions may be obtained in the internal space of the body by suction, possibly complemented by the addition of appropriate substances.

However, the known sampling device does not provide the conditions enabling a simple way of providing satisfactory preservation of the bacteria of the microbiota, and especially of the anaerobic bacteria, which are the majority components of the intestinal microbiota. Furthermore, the known sampling device does not make it possible to perform the necessary manipulations for sampling the microbiota in a safe way, the operator performing the manipulations running the risk of entering into contact with the biological matter.

The invention is directed to mitigating the problems raised above.

SUMMARY OF THE INVENTION

To that end, according to a first aspect, the invention provides a sampling method for sampling microorganisms contained in biological matter, the sampling method employing a sampling device of the aforementioned type wherein said at least one transfer member comprises an evacuation member configured for evacuating, in the open state, at least part of the gases contained in the internal space of the body of the container, the sampling method comprising the steps consisting of:

collecting the biological matter in the internal space of the body of the container, and closing the internal space by mounting the cover on the neck of the container, putting the internal space of the body of the container under anaerobiosis by putting the evacuation member in the open state, by compressing the body of the container so as to evacuate at least part of the gases contained in the internal space of the body of the container by putting the evacuation member in the closed state.

Thus, the invention enables optimal conditions for the preservation of microorganisms, and in particular the microbiota, to be obtained simply and safely. In particular, the invention enables placing under anaerobiosis to be performed by simple compression applied on the body of the container to evacuate the oxygen and preserve the anaerobic bacteria that are sensitive to oxygen. The bacteria maintained in a closed system may be kept in these conditions of anaerobiosis while being isolated from external contaminants. Furthermore, this placing under anaerobiosis as well as the later placing in suspension of the biological matter that are carried out by compressing the body of the container, without having recourse to a mixer, enable the viability of the bacteria to be enhanced. Furthermore, the manipulations may be carried out with the container closed by the cover and thus without risk of direct contact with the biological matter for the operator.

the evacuation member may have opposite internal and external faces, the evacuation member being in the closed state when at rest and passing into the open state when a difference of pressure is applied between the internal and external faces, the sampling method may then provide, during the step consisting of putting the internal space of the body of the container under anaerobiosis, of automatically putting the evacuation member in the open state by compressing the body of the container then automatically putting the evacuation member in the closed state by stopping compressing the body of the container.

the cover may comprise a bearing part having overall rigidity and the evacuation member may be provided in the bearing part of the cover. The sampling method may then provide, during the step consisting of putting the internal space of the body of the container under anaerobiosis, for pressing the body of the container against the bearing part of the cover.

The sampling method may further comprise the step consisting of suspending the biological matter by introducing a diluent fluid into the internal space of the body of the container via said at least one transfer member in the open state, and by mixing the biological matter and the diluent fluid by pressing on the body of the container.

The sampling method may further comprise the step consisting of sampling the microorganisms by collecting at least some of the biological matter suspended via said at least one transfer member in the open state.

The sampling method may provide, during the step consisting of collecting the biological matter in the internal space of the body of the container, for directly collecting the faecal matter by placing the sampling device on a toilet seat.

According to a second aspect, the invention provides a sampling device for sampling microorganisms contained in biological matter, the sampling device comprising:
  a container comprising a body which comprises an internal space configured to receive the biological matter, and a neck which delimits an access opening to the internal space of the body, the body of the container being constituted by a flexible bag,
  a cover configured to be removably and sealingly mounted on the neck of the container so as to obturate the access opening of the neck and close the internal space of the body,
  wherein at least one of the container and the cover is provided with at least one transfer member internally comprising a passage between the internal space and an external environment, the transfer member having an open state in which said transfer member establishes communication with the internal space through the passage, and a closed state in which said transfer member prevents all communication with the internal space through the passage,
  wherein said at least one transfer member comprises an evacuation member having opposite internal and external faces, the evacuation member being in the closed state when at rest and passing into the open state when a difference of pressure is applied between the internal and external faces, so as to automatically put the evacuation member in the open state by compressing the body of the container to evacuate at least part of the gases contained in the internal space of the body of the container and place the internal space of the body of the container under anaerobiosis, and to automatically put the evacuation member in the closed state by stopping compressing the body of the container.

To avoid spreading germs and thus ensure the safety of the manipulator, the evacuation member may comprise a microporous retaining membrane disposed in the passage and configured to retain the biological matter while allowing gases to pass Said at least one transfer member may comprise a connection port provided through one of the container and the cover and internally comprising at least part of the passage, and an obturating member movable relative to the connection port between an obturating position, in which said obturating member prevents all communication through the passage, and a freeing position in which said obturating member allows communication through the passage.

The obturating member may be mounted in the passage of the connection port, the obturating member being urged towards its obturating position and being movable towards the freeing position These provisions make it possible to make a connection simply and without boring, which is removable and fluid-tight and which, where required, enables bidirectional communication while maintaining the internal space entirely closed so long as the obturating member is not moved by a positive action towards the freeing position.

Said at least one transfer member may comprise at least one tube extending from the connection port and internally comprising part of the passage.

Said at least one transfer member may comprise at least one valve mounted on the tube, the valve being movable between a closed position, in which said valve prevents all communication through the passage, and an open position in which said valve allows the communication through the passage.

When the obturating member is mounted in the passage of the connection port, the tube may comprise a complementary connection port provided with a freeing member and which is configured to be removably connected to the connection port such that the freeing member moves the obturating member towards the freeing position.

The cover may comprise a bearing part having overall rigidity and the evacuation member may be provided in the bearing part of the cover, so as to be able to press the body of the container against the bearing part of the cover to put the internal space of the body of the container under anaerobiosis.

The sampling device may further comprise a filter attached to the container so as to define, in the internal space, an upper compartment into which the access opening opens, and a lower compartment, the filter having pores comprised between 0.1 mm and 1.5 mm.

In order to avoid obstruction of the passage by a solid body contained in the biological matter or sampling of such a solid body with the microorganisms, said at least one transfer member may be provided in the lower compartment, downstream of the filter relative to the access opening.

According to a third aspect, the invention concerns a sampling kit comprising:
  a sampling device as defined above, and
  at least one ancillary device chosen from a supply device configured to supply the internal space with fluid, and a receiving device configured to receive a fluid contained in the internal space, the ancillary device being in particular chosen from a reservoir of diluent fluid, an analysis tube, a distribution pipe and a collecting bag for microorganisms.

The sampling kit makes it possible in particular to sample and process the microorganisms into the form of an inoculum ready for use.

When the transfer member of the sampling device comprises an obturating member mounted in the passage of a connection port, the ancillary device may comprise a complementary connection port provided with a freeing member and which is configured to be removably connected to the connection port such that the freeing member moves the obturating member towards the freeing position.

BRIEF DESCRIPTION OF THE DRAWINGS

Other objects and advantages of the invention will appear on reading the following description of a specific embodiment of the invention given by way of non-limiting example, the description being made with reference to the accompanying drawings in which.

DETAILED DESCRIPTION OF THE INVENTION

Figure 1:
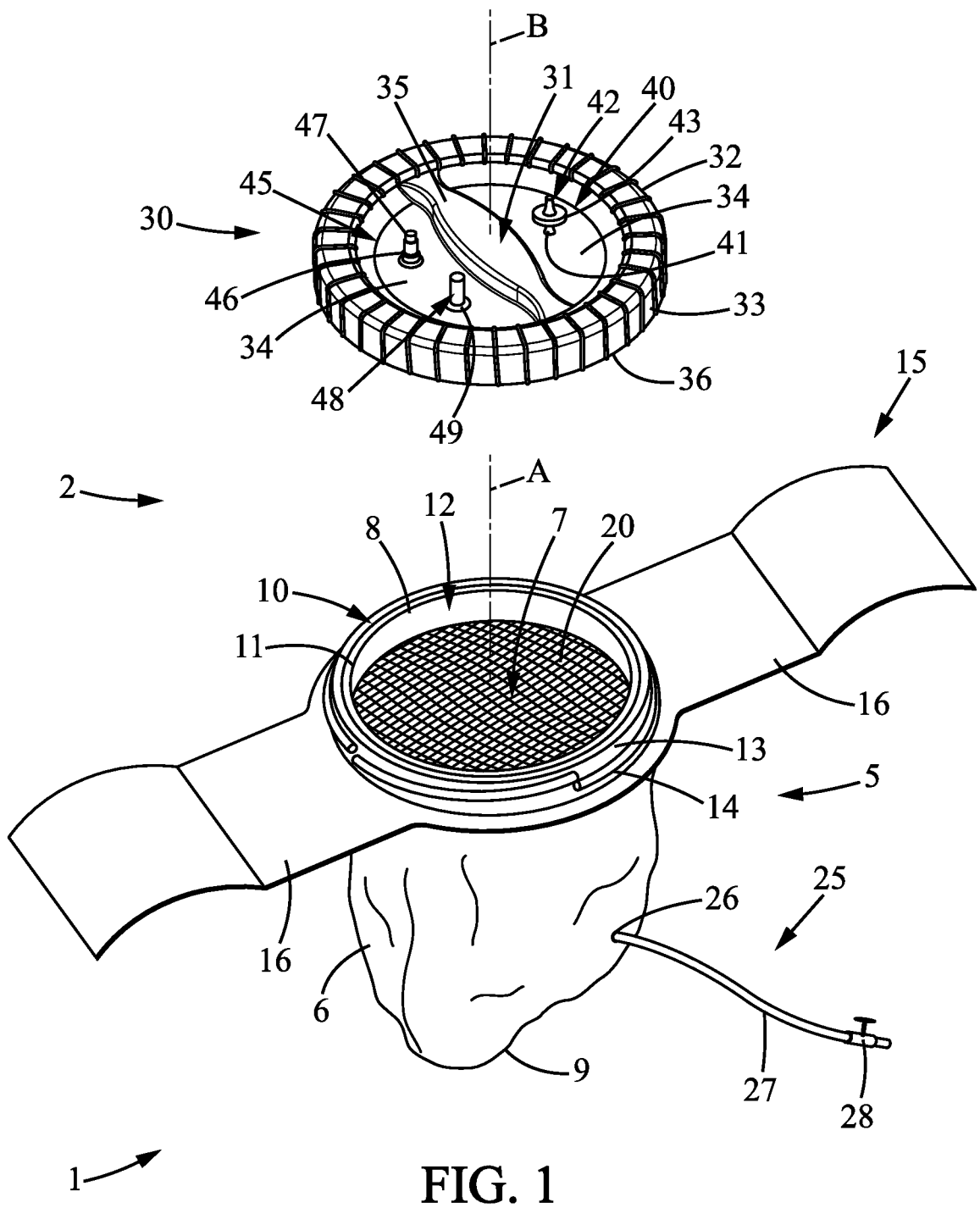
FIG. 1 is a representation in perspective of a sampling kit comprising a sampling device for sampling microbiota contained in a biological matter, the sampling device comprising a container and a cover, the container comprising a body constituted by a flexible bag and the cover being provided with an evacuation member configured to evacuate at least part of the gases contained in an internal space of the body of the container.

In the drawings, the same references designate identical or similar parts.

FIG. 1 represents an embodiment of a sampling kit 1 comprising a sampling device 2 for sampling microorganisms contained in biological matter. In the embodiment represented, without being limited thereto, the sampling device 2 is implemented in the sampling of intestinal microbiota contained in the faecal matter of an individual.

The sampling device 2 comprises a container 5 adapted in particular to collect faecal matter.

The container 5 comprises a body 6 constituted by a flexible bag delimiting an internal space 7 configured to receive the biological matter and having an upper edge 8. The body 6 is formed from a deformable material configured to form a barrier to the faecal matter contained in the internal space 7 and to external fluids in order to avoid any exchange between the faecal matter and the exterior. In particular, the body 6 may be produced from polyethylene (PE), polypropylene (PP), polyvinyl chloride (PVC), polycarbonate (PC) or ethylene-vinyl acetate (EVA).

The container 5 also comprises a cylindrical neck 10, defined by a solid of revolution about a central axis A, to which the upper edge 8 of the body 6 is joined by any appropriate means and in particular by welding, bonding or other means. The neck 10 has overall rigidity and is, for example, produced from plastic material such as polyethylene (PE), polypropylene (PP), polyvinyl chloride (PVC), polycarbonate (PC) or ethylene-vinyl acetate (EVA). The neck 10 has an internal surface 11 which delimits an access opening 12 to the internal space 7 of the body 6, and an external surface 13 provided with one or more ramps 14 arranged so as to form an external screw thread. As a variant, any other continuous or discrete arrangement of one or more ramps 14, which may be equally spaced, could be provided on the external surface 13 of the neck 10.

The container 5 also comprises a support 15 adapted to provide stable holding in an appropriate orientation, in particular with the access opening 12 upwardly oriented. In the embodiment represented, the support 15 is joined to the neck 10 and shaped so as to be able to come to bear on a rim of a toilet seat 3 in accordance with the application considered. The support 15 comprises two wings 16 extending radially relative to the central axis A in diametrically opposite directions from the external surface 13 of the neck 10. As a variant, according to the application, the support could have any other appropriate shape.

A filter 20 is joined, for example by welding, bonding or other method, to the container 5 so as to define, in the internal space 7, two compartments. In FIG. 1, the filter 20 is then joined to the body 6 so as to extend in the neighborhood of the access opening 12 of the neck 10. The internal space 7 then has an upper compartment into which opens the access opening 12 and a lower compartment in the region of the bottom 9. As a variant, the filter may be joined at any other appropriate location of the neck or of the body of the container to define lower and upper compartments of appropriate respective capacities. The filter has pores comprised between 0.1 mm and 1.5 mm, in particular between 0.3 mm and 0.5 mm, configured to retain insoluble solid bodies contained in the faecal matter.

The body 6 of the container 5 comprises a first transfer member forming, in the particular embodiment represented, a collecting member 25 enabling the microorganisms from the intestinal microbiota to be collected. The collecting member 25 comprises a lower connection port 26 formed through the body 6 of the container 5 in the neighborhood of the bottom 9 of the body 6, and a tube 27 extending from the lower connection port 26. The lower connection port 26 and the tube 27 thereby define a passage inside the collecting member 25 between the internal space 7 and an external environment. The collecting member 25 comprises a valve 28 mounted on the tube 27 and movable between:

a closed position defining a closed state of the collecting member 25 in which it prevents any communication, and in particular any fluid flow, through the passage, and an open position defining an open state of the collecting member 25 in which it allows communication, and in particular fluid flow, through the passage.

As a variant, the collecting member 25 could comprise several tubes 27 and several valves 28.

The tube 27 may be removably linked to the lower connection port 26. An obturating member in the form of a check valve may be mounted in the passage of the lower connection port 26 and be urged towards an obturating position, in which the obturating member prevents any communication through the passage, and be movable towards a freeing position in which the obturating member allows the communication through the passage. The tube 27 then comprises a complementary connection port configured to cooperate with the lower connection port 26. In particular, the complementary connection port is provided with a freeing member arranged to move the obturating member to the freeing position when the complementary connection port is connected to the lower connection port 26. The lower connection port 26 and the complementary connection port may then form, one being the male member and the other the female member, a Luer Lock type connection equipped with a check valve and in which:

- the lower connection port 26 is in the obturating position preventing any communication between the internal space 7 and the exterior through the passage when the tube 27 is separated from the body 6 of the container 5, and
- the lower connection port 26 is in the freeing position establishing communication between the internal space 7 and the exterior through the passage when the tube 27 is connected to the body 6 of the container 5.

Such a connection port makes it possible, by a connection without piercing, to form a two-directional communication through the passage while maintaining the internal space totally closed so long as the obturating member has not been moved towards the freeing position by the freeing member.

In another embodiment, the tube 27 of the collecting member 25 may be integrally formed with the lower connection port 26, the valve 28 then forming the obturating member movable relative to the connection port 26 between an obturating position corresponding to the closed position of the valve 28, and a freeing position corresponding to the open position. As a variant, instead of the valve 28, the obturating member could be a plug that can be pierced or that is removably mounted on a free end of the tube 27.

In order to be able to preserve the collected faecal matter, the sampling device 2 comprises a cover 30 adapted to be mounted removably and in fluid-tight manner on the neck 10 of the container 5 so as to obturate the access opening 12 of the neck 10 and to close the internal space 7 of the body 6. The cover 30 has overall rigidity and is, for example, formed from a plastic material similar to that of the neck 10. It comprises a transverse wall 31 extending perpendicularly to the central axis B and having a circular peripheral edge 32 with a diameter corresponding to that of the neck 10 of the container 5. The cover 30 also comprises a cylindrical skirt 33, defined as a solid of revolution about the central axis B, which extends from the peripheral edge 32 of the transverse wall 31. The skirt 33 has an internal surface provided with projections which, according to requirement, form an internal screw thread, and which are configured to cooperate with the ramps 14 on the external surface 13 of the neck 10. As a variant, any other device enabling the cover 30 and the neck 10 of the container 5 to be joined removably and in a fluid-tight manner could be provided, in particular a clipping device. The transverse wall 31 has an upper surface having two recesses 34 arranged on respective opposite sides of a central projection 35 for grasping. The recesses 34 are such that a lower surface of the transverse wall 31 at the location of the recesses 34 is flush with or extends beyond a free edge 36 of the skirt 33.

In one of the recesses 34, the cover 30 is provided with a second transfer member produced in the form of an evacuation member configured, in an open state, to evacuate at least part of the gases contained in the internal space 7 of the body 6 of the container 5. In the particular embodiment represented, the evacuation member is a one-way valve 40 which is in a closed state at rest, when not acted upon externally, and which passes to an open state when a difference of pressure is applied between opposite internal and external faces, respectively situated at the internal and external surfaces of the cover 30.

In particular, the one-way valve 40 comprises an upper connection port 41, formed through the cover 30, between its lower and upper surfaces, and a tube 42 extending from the upper connection port 41. The upper connection port 41 and the tube 42 thereby define a passage inside the one-way valve 40 between the internal space 7 and the external environment. In a central bead 43, the tube 42 of the one-way valve 40 comprises a microporous retaining membrane disposed in the passage and which is configured to retain the biological matter while enabling gases to pass. The microporous retaining membrane may in particular be of the type commercialized by POREX® FILTRATION under the reference XS-49 110 made of polypropylene with pores comprised between 125 µm and 175 µm. As a variant, the microporous retaining membrane could be produced in any other appropriate way and in particular of a sintered material having pores comprised between 100 µm and 350 µm, in particular between 200 µm and 300 µm, for example 250 µm.

An obturating member in the form of a check valve may be mounted in the passage of the one-way valve 40 and be urged towards an obturating position, preventing any communication through the passage, and be movable towards a freeing position allowing communication through the passage.

In the embodiment shown, the tube 42 of the one-way valve 40 is integrally formed with the upper connection port 41. The obturating member may be provided in the tube 42, in particular in the neighborhood of a free end.

In another embodiment, the tube 42 of the one-way valve 40 may be removably connected to the upper connection port 41. In addition to or instead of the check valve provided in the tube 42, a new obturating member in the form of a check valve may be provided in the upper connection port 41 and be urged towards an obturating position, preventing any communication through the passage, and be movable towards a freeing position allowing communication through the passage. In the this other embodiment, the tube 42 comprises a complementary connection port adapted to cooperate with the upper connection port 41. In particular, the complementary connection port is provided with a freeing member arranged to move the check valve of the upper connection port 41 to the freeing position when the complementary connection port is connected to the upper connection port 41. The upper connection port 41 is in the obturating position when the tube 42 is separated from the cover 30 and in the freeing position when the tube 42 is connected to the cover 30.

As a variant, the evacuation member could be formed in any appropriate way other than a one-way valve. In particular, the evacuation member could comprise a passage able to be obturated by an obturating member in the form of a plug removably placed in the passage, for example by being removably mounted on the free end of the tube 42. When the plug is removed from the passage, the evacuation member is in the open state, in which communication between the internal space 7 of the container 5 and the exterior is established through the passage. When the plug is placed in the passage, it obturates the passage and the evacuation member is in a closed state, in which any communication between the internal space 7 of the container 5 and the exterior through the passage is prevented.

In the other recess 34, the cover 30 comprises third and fourth transfer members which respectively form, in the particular embodiment shown, a supply member 45 and a sampling member 48. The supply member 45 and sampling member 48 are each adapted to establish communication between the internal space and the exterior in the open state, and to close the communication between the internal space and the exterior in the closed state.

The supply members 45 and sampling member 48 respectively comprise additional upper connection ports 46, 49 for ancillary devices of the sampling kit.

Each of the additional upper connection ports 46, 49 is formed through the cover 30, between the lower and upper surfaces, to constitute one of the members, for example female, of a Luer Lock type connection. As was described above, each of the additional upper connection ports 46, 49 of the supply member 45 and sampling member 48 may be provided with an obturating member produced in the form of a check valve 47, a plug or other member.

The obturating member of the supply member 45 is, for example, produced in the form of a check valve 47 mounted in the passage and configured to cooperate with a freeing member of a complementary connection port provided on the ancillary device and constituting the other member, for example male, of the Luer Lock type connection. The check valve 47 urged towards an obturating position preventing any communication through the passage places the additional upper connection port 46 of the supply member 45 in a closed state when the ancillary device is separated from the cover 30. The obturating member 47 moved to a freeing position permitting communication through the passage places the additional upper connection port 46 of the supply member 45 in an open state when the ancillary device is connected to the cover 30.

The obturating member of the sampling member 48 is, for example, produced in the form of a plug, not shown, removably mounted on the additional upper connection port 49. The sampling member 48 is in an open state promoting communication through the passage when the plug is separated from the additional upper connection port 49, and a closed state preventing any communication through the passage when the plug is on the additional upper connection port 49.

The ancillary devices may in particular comprise:
one or more reservoirs of diluent fluid, and in particular a supply bag, configured to be connected to the additional upper connection port 46 of the supply member 45, the reservoir comprising, where required, a pipe equipped with a complementary connection port with a freeing member.
one or more analysis tubes configured to be connected to the additional upper connection port 49 of the sampling member 48, each analysis tube extending between an open end provided, where required, with a complementary connection port with a freeing member, and a closed end so as to be able to extract faecal matter for analysis purposes, and
one or more bags for collecting microorganisms configured to be connected to the lower connection port 26 of the collecting member 25 via a distribution duct comprising one or more pipes equipped with a complementary connection port with a freeing member and, where required, with one or more valves.

As a variant, the sampling kit 1 could comprise any other type of ancillary device chosen from a supply device configured to supply the internal space 7 with fluid, and a receiving device configured to receive a fluid contained in the internal space 7.

The invention has been described with a sampling device comprising first, second, third and fourth transfer members respectively constituting a collecting member, an evacuation member in the form of a one-way valve, a supply member and a sampling member. As a variant, it would be possible to provide any other arrangement, any other embodiment and any other functionality with one or more transfer members internally comprising a passage and of which at least one forms an evacuation member configured, in the open state, to evacuate at least part of the gases contained in the internal space of the body of the container. In particular, the sampling device 2 could comprise only the first 25 and second 40 transfer members described earlier or for instance only one of them. At least one transfer member is provided, preferably in the lower compartment, downstream of the filter relative to the access opening, in order to avoid obstruction of the connection port by a solid body contained in the biological matter or a sample of such a solid body with the microorganisms.

A method of sampling microbiota contained in biological matter implementing the sampling system will now be described in relation with FIGS. 2 to 4.

Figure 2:
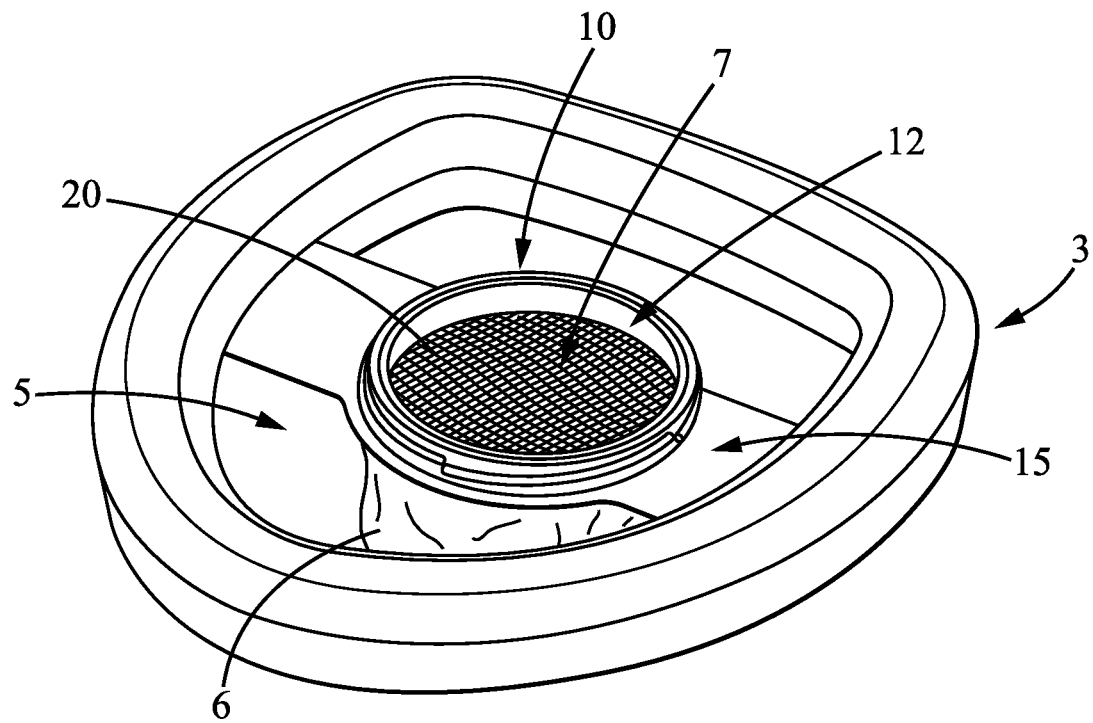
FIG. 2 is a representation in perspective of the sampling device of FIG. 1 in an application for sampling intestinal microbiota contained in faecal matter such as biological matter, the sampling device being open with the cover separate from the container for collecting the faecal matter.

In FIG. 2, faecal matter is collected by placing the container 5 of the sampling device 2 on the toilet seat 3 with the wings resting on the rim of the toilet seat 3. As a variant, the faecal matter could be deposited in any other appropriate way in the internal space 7 of the container 5. During this collecting step, the tube 27 may be separated from the container 5.

Figure 3:
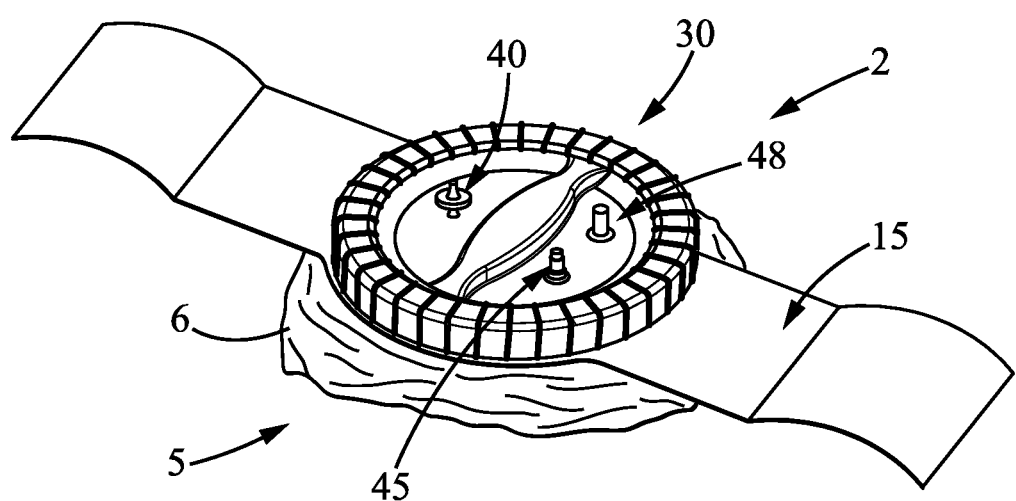
FIG. 3 is a representation in perspective of the sampling device of FIG. 1 placed in a condition of anaerobiosis with the cover mounted on the container and the body pressed against the cover to evacuate the oxygen from the internal space of the body and preserve the microbiota present in the collected faecal matter.
Figure 4:
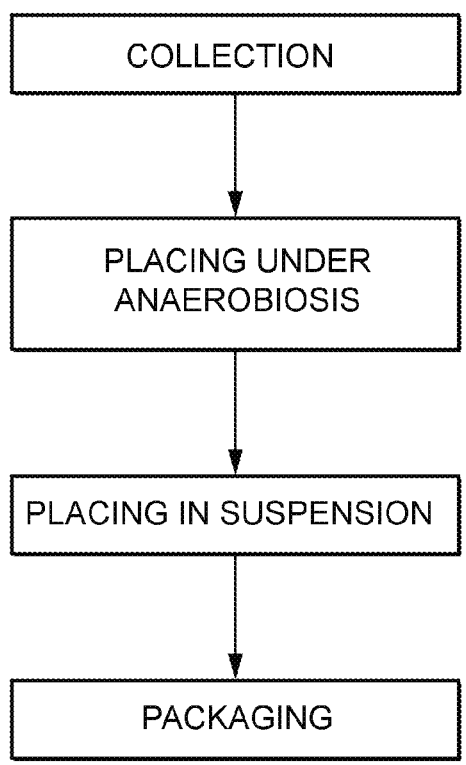
FIG. 4 is a flowchart illustrating steps of a method of sampling microbiota contained in biological matter, the sampling method implementing the sampling device of FIG. 1.

In FIG. 3, once the faecal matter has been received on the filter 20 in the internal space 7 of the body 6, the internal space 7 is closed by screwing the cover 30 onto the neck 10 of the container 5. The collecting member 25, the one-way valve 40 and the two sampling members 45, 48 are in the closed state. An operator may then proceed with placing the internal space 7 of the body 6 of the container 5 under anaerobiosis by compressing the body 6 of the container 5 thereby automatically passing the one-way valve 40 into the open state. In particular, the transverse wall 31 of the cover 30 at the location of the recesses 34 forms a bearing part against which the body 6 of the container 5 can be pressed when the cover 30 is mounted on the neck 10 of the container 5. In doing this, part of the gases contained in the internal space 7 of the body 6 of the container 5, and in particular the oxygen, is evacuated through the one-way valve 40 provided in the bearing part of the cover 30. The compression of the body 6 may be improved by a grip or rest on a gripping member, such as a rigid plate or a handle, arranged on a base 9 at the remote opposite to the upper edge 8. Once the compression of the body 6 of the container 5 is stopped, the one-way valve 40 automatically passes back to the closed state to maintain the anaerobic conditions in the internal space 7 of the body 6.

According to the application considered, the placing under anaerobiosis may be completed by an injection of inert gas into the internal space 7 of the body 6 of the container 5 via one of the transfer members 25, 40, 45, 48.

After a possible waiting time under determined conditions and possible visual inspection, the faecal matter is placed in suspension by connecting the reservoir of diluent fluid, such as a bag of diluent fluid or a bottle of diluent fluid, to the additional upper connection port 46 of the supply member 45 on the cover 30 of the sampling device 2. The additional upper connection port 46 passes from the open state such that the diluent fluid is introduced into the internal space 7 of the body 6 of the container 5. The biological matter and the diluent fluid are then mixed by pressing on the body 6 of the container 5. The homogeneity of the suspension is improved by its passage through the filter 20.

Prior to the placing in suspension of the faecal matter, complementary analyses may be performed on a sample taken via an analysis tube connected to the additional upper connection port 49 of the sampling member 48 on the cover 30 of the sampling device 2. As a variant, the sampling of such a sample may be performed simultaneously or subsequently to the placing in suspension.

To process the microbiota into the form of an inoculum ready for use, the tube 27 or a distribution duct may be connected to the lower connection port 26 of the collecting member 25 to take off the microbiota contained in the faecal matter to one or more collecting bags respectively connected to one or more pipes of the distribution duct.

The microbiota may then undergo any appropriate operation for its preservation, possible transport and its transplantation.

The invention claimed is:

1. A sampling method for sampling microorganisms contained in biological matter, the sampling method comprising the steps of:
    collecting a biological matter in an internal space (7) of a body (6) of a container (5), and closing the internal space (7) by mounting a cover (30) on a neck (10) of the container (5);
    compressing the body (6) of the container (5) to put an evacuation member (40), which comprises a one-way valve having opposite internal and external faces, in an open state by the difference in pressure applied between the internal and external faces so as to evacuate at least part of gases contained in the internal space (7) of the body (6) of the container (5) and to put the internal space (7) of the body (6) of the container (5) under anaerobiosis; and then
    stop compressing the body (6) of the container (5) to put the evacuation member (40) in the closed state at rest,
    wherein the sampling method employs a sampling device (2) comprising:
        the container (5) configured to receive the biological matter, the container (5) comprising a neck (10) which delimits an access opening (12) to the internal space (7) of the body (6), the body (6) of the container (5) being constituted by a flexible bag, and
        the cover (30) configured to be removably and sealingly mounted on the neck (10) of the container (5) so as to obturate the access opening (12) of the neck (10) and close the internal space (7) of the body (6),
    wherein at least one of the container (5) and the cover (30) is provided with at least one transfer member (25, 40, 45, 48) internally comprising a passage between the internal space (7) and an external environment, the transfer member (25, 40, 45, 48) having an open state in which said transfer member (25, 40, 45, 48) establishes communication with the internal space (7) through the passage, and a closed state in which said transfer member (25, 40, 45, 48) prevents all communication with the internal space (7) through the passage, said at least one transfer member (25, 40, 45, 48) comprising the evacuation member (40) configured for evacuating, in the open state, at least part of the gases contained in the internal space (7) of the body (6) of the container (5), and
    wherein the evacuation member (40) has opposite internal and external faces, the evacuation member comprising a one-way valve being in the closed state when at rest and oriented to pass into the open state when a difference of pressure is applied between the internal and external faces.

2. The sampling method according to claim 1, wherein the cover (30) comprises a bearing part (31) having overall rigidity and wherein the evacuation member (40) is provided in the bearing part (31) of the cover (30),
    wherein the step of compressing the body (6) comprises pressing the body (6) of the container (5) against the bearing part (31) of the cover (30).

3. The sampling method according to claim 1, further comprising the step of
    suspending the biological matter by introducing a diluent fluid into the internal space (7) of the body (6) of the container (5) via said at least one transfer member (25, 40, 45, 48) in the open state, and
    mixing the biological matter and the diluent fluid by pressing on the body (6) of the container (5).

4. The sampling method according to claim 3, further comprising the step of
    sampling the microorganisms by collecting at least some of the biological matter suspended via said at least one transfer member (25, 40, 45, 48) in the open state.

5. The sampling method according to claim 1, wherein the step of collecting the biological matter in the internal space (7) of the body (6) of the container (5) comprises directly collecting the fecal matter by placing the sampling device on a toilet seat (3).

\* \* \* \* \*